United States Patent [19]

Jensen

[11] Patent Number: 4,642,402
[45] Date of Patent: Feb. 10, 1987

[54] PROCESS FOR CONVERSION OF LIGHT ALIPHATIC HYDROCARBONS TO AROMATICS

[75] Inventor: Robert H. Jensen, Clarendon Hills, Ill.

[73] Assignee: UOP Inc., Des Plaines, Ill.

[21] Appl. No.: 814,830

[22] Filed: Dec. 30, 1985

[51] Int. Cl.$^4$ .............................................. C07C 12/02
[52] U.S. Cl. ..................................... 585/411; 585/415
[58] Field of Search ................................ 585/411, 415

[56] References Cited

U.S. PATENT DOCUMENTS

| 2,992,283 | 7/1961 | Eng | 260/673 |
| 3,761,389 | 9/1973 | Rollman | 208/64 |
| 4,180,689 | 12/1979 | Davies et al. | 585/407 |
| 4,329,532 | 5/1982 | Conn et al. | 585/407 |
| 4,347,394 | 8/1982 | Detz et al. | 585/419 |
| 4,444,988 | 4/1984 | Capsuto et al. | 585/415 |
| 4,528,412 | 7/1985 | Steacy | 585/415 |

OTHER PUBLICATIONS

Csicsery, Sigmund M., "Dehydrocyclodimerization", *Ind. Eng. Chem. Process Des. Dev.*, vol. 18, No. 2, 1979, pp. 191–197.

*Primary Examiner*—Curtis R. Davis
*Attorney, Agent, or Firm*—Thomas K. McBride; John F. Spears, Jr.

[57] ABSTRACT

A process is disclosed for the dehydrocyclodimerization of light aliphatic hydrocarbons into aromatic hydrocarbons. The process provides improved per pass conversion and an improved yield structure by increasing the relative percentage of xylene which is produced as compared to benzene. This improvement is achieved by recycling benzene recovered from the reaction zone effluent to the reaction zone.

19 Claims, 1 Drawing Figure

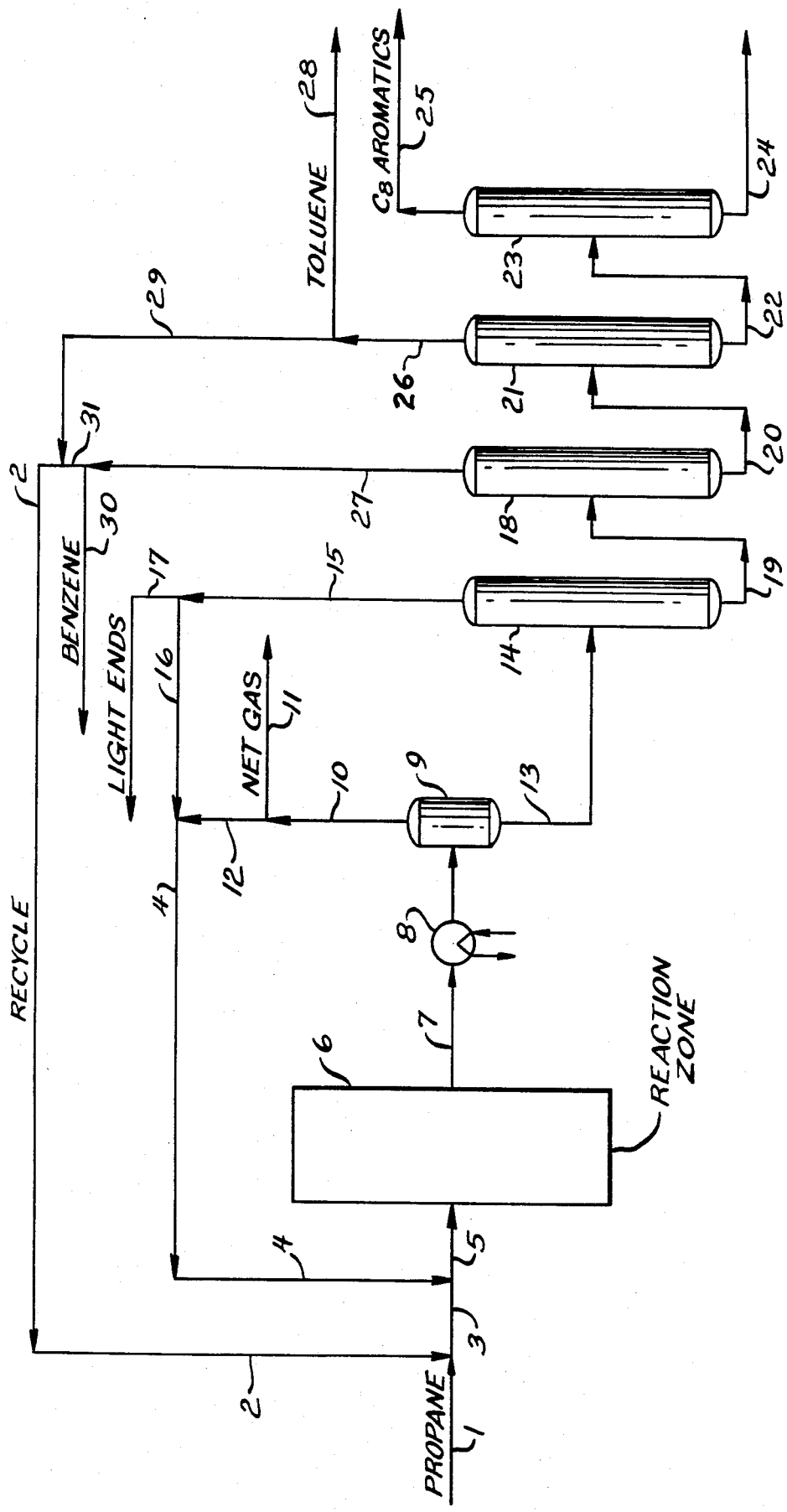

PROCESS FOR CONVERSION OF LIGHT ALIPHATIC HYDROCARBONS TO AROMATICS

FIELD OF THE INVENTION

The subject process relates to a hydrocarbon conversion process. Specifically, the subject process relates to a catalytic process referred to as dehydrocyclodimerization wherein two or more molecules of a light aliphatic hydrocarbon, such as propane or propylene, are joined together to form a product aromatic hydrocarbon. Nonaromatic hydrocarbons are also produced, especially when substantial amounts of olefins are present in the feed. The invention specifically relates to the separatory methods used to recover hydrogen and product $C_6$-plus hydrocarbons from a vapor phase reaction zone effluent stream. This separatory method also relates to techniques for recycling unconverted feed hydrocarbons to the reaction zone.

INFORMATION DISCLOSURE

There are a large number of references which describe the conversion of light aliphatic hydrocarbons to aromatic hydrocarbons. For instance, U.S. Pat. No. 2,992,283 issued to J. Eng describes the conversion of propylene to a variety of higher molecular weight hydrocarbons using a treated crystalline aluminosilicate as the catalyst. U.S. Pat. No. 4,347,394 issued to C. M. Detz et al describes the conversion of $C_5$-plus hydrocarbons to aromatics using a nonacidic zeolite supporting a platinum compound. U.S. Pat. No. 4,329,532 issued to P. J. Conn et al describes the conversion of $C_4$-minus olefins or mixtures of olefins and paraffins to aromatic hydrocarbons. The catalyst comprises a crystalline silicate having a specified composition, crystallite size range, and X-ray diffraction pattern. U.S. Pat. No. 4,444,988 issued to L. M. Capsuto et al describes a process flow for the recovery of the products of a similar process consuming a $C_2$-$C_5$ olefinic feedstock. The emphasis of this patent is the use of heat exchange to improve the economics of condensing hydrocarbons from the reaction zone effluent stream.

U.S. Pat. No. 4,180,689 issued to E. E. Davies et al describes the conversion of $C_3$-$C_8$ aliphatic hydrocarbons to aromatic hydrocarbons in a process which employs a catalyst comprising gallium supported on an aluminosilicate. U.S. Pat. No. 3,761,389 issued to L. D. Rollman et al describes an improved process for converting $C_2$ to 400° F. hydrocarbons to aromatics over a ZSM-5 type catalyst. The improvement resides in the use of two reaction stages in series, with the first being at more severe operating conditions. U.S. Pat. No. 4,528,412 issued to P. C. Steacy also describes catalyst, reaction zone operations and product recovery methods for dehydrocyclodimerization processes. A review of dehydrocyclodimerization is presented at page 191 of Vol. 18, No. 2, 1979 issue of "Industrial Engineering Chemistry—Process Design and Development".

BRIEF SUMMARY OF THE INVENTION

The invention is a unique process flow which increases the yield of more valuable alkylaromatic hydrocarbons in a dehydrocyclodimerization process. It has also been discovered that the invention yields the unexpected result of a higher per pass conversion of the feed light hydrocarbon. The invention is characterized by the passage of benzene and/or toluene into the dehydrocyclodimerization reaction zone in admixture with feed light hydrocarbons. A limited embodiment of the invention features the recycling of benzene and/or toluene recovered from the reaction zone effluent stream.

A broad embodiment of the invention may be characterized as a process which comprises the steps of passing a first process stream comprising benzene and a feedstream comprising a $C_2$-$C_5$ aliphatic feed hydrocarbon into a reaction zone maintained at dehydrocyclodimerization conditions and containing a solid catalyst and producing a reaction zone effluent stream which comprises the feed hydrocarbon, benzene, toluene and xylenes; and, separating the reaction zone effluent stream in a separation zone and producing a product stream comprising xylenes.

BRIEF DESCRIPTION OF THE DRAWING

The drawing is a simplified process flow diagram of a preferred embodiment of the invention showing the production of $C_8$ aromatics from propane with benzene being recycled.

DETAILED DESCRIPTION

Processes for the conversion of light aliphatic hydrocarbons to aromatic or nonaromatic $C_6$-plus hydrocarbons have been the subject of significant development efforts as evidenced by the previously cited references. The basic utility of the process is the conversion of the low cost and highly available $C_3$ and/or $C_4$ hydrocarbons into more valuable aromatic hydrocarbons and hydrogen or to convert the feed hydrocarbons to higher molecular weight aliphatic products. This may be desired simply to upgrade the value of the hydrocarbons. It may also be desired to correct an overabundance of the $C_3$ and $C_4$ hydrocarbons or to fulfill a need for the aromatic hydrocarbons. The aromatic hydrocarbons are highly useful in the production of a wide range of petrochemicals, with benzene being one of the most widely used basic feed hydrocarbon chemicals. The product aromatic hydrocarbons are also useful as blending components in high octane number motor fuels.

The feed compounds to a dehydrocyclodimerization process are light aliphatic hydrocarbons having from 2 to 4 carbon atoms per molecule. The feed stream may comprise a single compound or a mixture of two or more of these compounds. The preferred feed compounds are propane, propylene, the butanes, and the butylenes, with saturates being highly preferred. The feed stream to the process may also contain some $C_2$ and $C_5$ hydrocarbons. It is preferred that the concentration of $C_5$ hydrocarbons in the feed stream to a dehydrocyclodimerization process is held to the minimum practical level, preferably below 5 mole percent. The preferred products of the process are $C_6$-plus aromatic hdyrocarbons. However, dehydro-cyclodimerization processes are not 100% selective and some nonaromatic $C_6$-plus hydrocarbons are produced even from saturate feeds. When processing a feed made up of propane and/or butanes, the very great majority of the $C_6$-plus product hydrocarbons will be benzene, toluene, and the various xylene isomers. A small amount of $C_9$-plus aromatics is also produced. The presence of olefins in the feed stream results in increased production of $C_6$-plus long chain hydrocarbons as products with the preferred catalyst system. Sizable olefin concentrations in the feed significantly decrease the production of aromatics.

The subject invention is directed to increasing the amount of the more valuable $C_8$ alkylaromatics, specifically xylenes, which are produced in a dehydrocyclodimerization reaction zone. The configuration of the reaction zone and the composition of the catalyst employed within the reaction zone are not basic elements of the invention or limiting characteristics of the invention. Nevertheless, in order to provide a background to the subject invention, it is felt useful to describe the preferred reactor system for use in the invention. This system comprises a moving bed radial flow multi-stage reactor such as is described in U.S. Pat. Nos. 3,652,231; 3,692,496; 3,706,536; 3,785,963; 3,825,116; 3,839,196; 3,839,197; 3,854,887; 3,856,662; 3,918,930; 3,981,824; 4,094,814; 4,110,081; and 4,403,909. These patents also describe catalyst regeneration systems and various aspects of moving catalyst bed operations and equipment. This reactor system has been widely employed commercially for the reforming of naphtha fractions. Its use has also been described for the dehydrogenation of light paraffins.

The preferred moving bed reactor system employs a spherical catalyst having a diameter between about 1/64 (0.04 cm) and ⅛ (0.32 cm) inch. The catalyst preferably comprises a support material and a metallic component deposited on the support material as through impregnation or coprecipitation. The previously cited references point out that the current trend is the use of a zeolitic support material, with the catalyst referred to in the art as a ZSM-5 type zeolite often being specified as a preferred material. When properly formulated, it appears this zeolitic material by itself has significant activity for the dehydrocyclodimerization reaction. Further information on such zeolitic catalysts for the DHCD reaction can be obtained by reference to European Patent Application No. 83 201 1422.9 by E. P. Kieffer. However, it is still preferred to employ a metallic component within the catalyst system to increase the activity of the catalyst. The preferred metallic component is gallium as described in the previously cited U.S. Pat. No. 4,180,689. A dehydrocyclodimerization reaction zone is preferably operated at a temperature between about 950°–1050° F. (487°–565°C.) and a pressure under 100 psig (689 kPag). Hydrogen-producing reactions are normally favored by lower pressures, and pressures under about 70 psig (483 kPag) at the outlet of the reaction zone are highly preferred.

The drawing illustrates the preferred embodiment of the invention. Those skilled in the art will recognize that this process flow diagram has been simplified by the elimination of many pieces of process equipment including some heat exchangers, process control systems, pumps, fractionation column overhead and reboiler systems, etc. which are not necessary to an understanding of the process. It may also be readily discerned that the process flow presented in the drawing may be modified in many aspects without departing from the basic overall concept of the invention. For example, the depiction of required heat exchangers in the drawing have been held to a minimum for purposes of simplicity. Those skilled in the art will recognize that the choice of heat exchange methods employed to obtain the necessary heating and cooling at various points within the process is subject to a large amount of variation as to how it is performed. In a process as complex as this, there exists many possibilities for indirect heat exchange between different process streams. Depending on the specific location and circumstance of the installation of the subject process, it may also be desired to employ heat exchange against steam, hot oil, or process streams from other processing units not shown on the drawing.

Referring now to the drawing, a feedstream comprising propane is passed into the process through line 1 and is combined with a recycle aromatic hydrocarbon stream carried by line 2. This admixture of the feed propane and the recycled aromatic hydrocarbons flows through line 3 for admixture with recycle hydrogen-rich gas from line 4. The admixture of hydrogen, feed propane and recycled aromatic hydrocarbons enters the reaction zone 6 through line 5. Within the reaction zone, these materials are contacted with a solid dehydrodimerization catalyst at the properly maintained reaction conditions to effect a conversion of at least a substantial amount of the entering propane into product aromatic hydrocarbons. There is also produced during this reaction a significant quantity of hydrogen and, as by-products of the reaction, a much smaller amount of methane and ethane.

There is thereby produced a reaction zone effluent stream carried by line 7 which comprises an admixture of residual amounts of the feed propane, the light by-product methane and ethane, the product aromatic hydrocarbons, recycled aromatic hydrocarbons, and hydrogen. The reaction zone effluent stream is passed through a heat recovery heat exchanger, which will typically be located within the reaction zone proper, and is then passed through a cooling zone such as the indirect heat exchange means 8. The resulting cooling should be sufficient to effect a partial condensation of the reaction zone effluent stream such that at least 85 mole percent of the $C_6+$ hydrocarbons are condensed. The resulting mixed phase reaction zone effluent stream is passed into a vapor-liquid separation zone 9. A light gas stream comprised mainly of propane, hydrogen and light hydrocarbons is removed from the separation zone 9 in line 10. A portion of the gas stream of line 10 is removed from the process through line 11 as a net gas stream at a rate set to balance the production of hydrogen and/or light hydrocarbons with its net rate of removal from the process. The remaining portion of the gas stream flows through line 12 for passage into line 4 and return to the reaction zone as a recycle gas stream. A gas purification zone may be located in either lines 10 or 12, if desired, to remove hydrocarbons from the gas stream and increase the hydrogen concentration of the net gas stream or the recycle gas stream.

The liquid phase condensate collected in the vapor-liquid separation vessel 9 is withdrawn through line 13 and passed into a first fractionation column 14 operated as a stripping column to remove undesired light hydrocarbons and dissolved hydrogen from the entering stream of condensate. The composition of the material removed overhead from column 14 will be dependent upon the desired composition of the overhead stream of the immediately downstream fractionation column 18. The stripping column 14 is preferably operated as a depentanizer column such that essentially all $C_5$-hydrocarbons which enter column 14 are removed from the column as a part of the net overhead stream of line 15. This will normally be the case when it is desired to produce high-purity benzene suitable for use as a petrochemical feed stock. However, if it is merely desired to utilize the produced aromatic hydrocarbons as a motor fuel blending component, the $C_5$ hydrocarbons present in the condensate of line 13 may be allowed to exit as a portion of the net bottoms stream of column 14. In this instance, the stripping column would be operated as a depropanizer or a debutanizer. In any instance, the rejected light hydrocarbons of the overhead stream of column 14 are removed in line 15 and may be divided if so desired into a recycled portion carried by line 16 and a product stream comprising light ends discharged from the process through line 17. It is contemplated that all of the light ends of line 15 could be recycled through line 16.

The net bottoms stream of column 14 will preferably comprise all of the $C_6+$ hydrocarbons present in the condensate fed to column 14. This stream is passed through line 19 into a column referred to herein as a benzene column. The function of the benzene column is to concentrate essentially all of the entering benzene into a net overhead stream withdrawn through line 27. At least a portion of this benzene is withdrawn through line 30 as a first product stream of the process. The remaining smaller amount of benzene is passed through line 31 into line 2 for recycling to the reaction zone. The net bottoms stream of column 18 is removed in line 20 and comprises substantially all of the $C_7+$ hydrocarbons charged to column 18. This bottoms stream is fed into a toluene column 21. The function of the toluene column is to concentrate essentially all of the entering toluene into a net overhead stream removed through line 26. Preferably, all of the toluene flowing through line 26 is withdrawn from the process through line 28 as a product stream. Alternatively, a portion of the toluene may be recycled through optional line 29 for passage into the reaction zone via line 2.

The net bottoms stream of column 21 will comprise substantially all of the $C_8+$ hydrocarbons entering the toluene column. This net bottoms stream is passed through line 22 into a $C_8$ product column 23. This column functions to separate the entering hydrocarbons into a $C_8$ rich net overhead stream carried by line 25 comprising $C_8$ aromatic hydrocarbons such as ortho-, meta-, and paraxylene. The remaining $C_9+$ aromatic hydrocarbons produced in the reaction zone are withdrawn from the process as a net bottoms stream carried by line 24. This mode of fractionation will normally be employed when it is desired to recover a relatively pure stream of the $C_8$ aromatics. This will be the case in most petrochemical applications. However, the final product stream of the process could comprise the bottoms stream of the toluene column 21 and would therefore comprise an admixture of $C_8$ and $C_9+$ aromatic hydrocarbons.

It is believed that those skilled in the art of petroleum and petrochemical process design may determine proper operating conditions, vessel designs, and operating procedures for the subject process through the use of standard process design techniques after having now been appraised of the overall flow of the process. These design techniques should include a recognition that it is undesirable to pass compounds which may tend to freeze or otherwise solidify into any low temperature portion of the process. For this reason, a drying zone may be provided. The function of this drying zone would be to prevent the passage of water into the low temperature equipment used to obtain a high purity hydrogen off gas stream. The drying zone is basically required to remove the small amount of water which may be dissolved within the feed stream to the process and/or any water which may be present on regenerated catalyst passed into the process or released from stripping steam used to seal catalyst passageways, etc.

The vapor-liquid separation zones employed within the process preferably comprise a suitably sized vertically oriented vessel having a demisting pad or other liquid entrainment removal means provided at the upper end. The fractionation zones employed in the process preferably contain trayed fractionation columns having sieve-type trays and being of relatively standard design. For instance, a properly designed column having 40 trays will function as the stripping column 14. Multicolumn fractionation zones of different configurations may of course be employed to recover specific product streams if so desired. It may, for instance, be designed to perform an initial split of the effluent stream or to remove a heavy hydrocarbon in one of the first columns. Suitable fractionation zones may be readily designed by those skilled in the art. The operating conditions required in the fractionation zones are dependent upon the compounds being separated and the desired separation. As used herein, the term "rich" is intended to indicate a concentration of the specified compound or class of compounds in excess of 65 mole percent.

This subject invention may be accordingly characterized as a dehydrocyclodimerization process which comprises the steps of passing a feedstream which comprises a $C_3$ or $C_4$ aliphatic hydrocarbon and a first process stream which comprises benzene into a dehydrocyclodimerization reaction zone maintained at dehydrocyclodimerization conditions and containing a solid catalyst comprising a zeolite and producing a reaction zone effluent stream comprising benzene, toluene and xylenes; separating the reaction zone effluent stream by a series of steps comprising partial condensation and fractional distillation and producing a product stream comprising xylenes and a second process stream comprising benzene; and, recycling at least a portion of the second process stream to the reaction zone as the previously referred to first process stream.

In the subject process, benzene is charged to the reaction zone in which a light aliphatic hydrocarbon is converted to benzene and other aromatic hydrocarbons. Preferably, the benzene is recycled from the reaction zone effluent as shown in the Drawing. However, there may be instances when it is economically advantageous to feed benzene from another source to the reaction zone rather than separating benzene from the reaction zone effluent. As is also shown in the Drawing, it is also contemplated that toluene may be recycled to the reaction zone in admixture with the feed hydrocarbons. It is preferred that the amount of benzene charged to the reaction zone with the feedstream will provide an aromatic hydrocarbon concentration in the feedstream ranging from about 1.0 to about 10 mole percent. Preferably, the concentration of the aromatic hydrocarbon in the feedstream is from about 2.5 to about 8 mole percent.

The subject process provides two separate advantages. First of all, the practice of the subject process has been shown by experiment to surprisingly increase the per pass conversion of a light aliphatic feed material to aromatics. Secondly, the subject process may be employed to shift the product alkylaromatic hydrocarbons distribution by increasing the amount of alkylbenzenes produced relative to benzene. These $C_8$ alkylbenzenes are normally a preferred product of a dehydrocyclodimerization process. For instance, they have octane numbers above that of benzene. They may also be a more desirable component of a gasoline boiling range motor fuel when it is desired to minimize the benzene content of the gasoline. In a petrochemical complex, the value of $C_8$ aromatics such as xylenes is normally significantly higher than the value attached to benzene. The practice of the subject invention will therefore offer significant economic benefits when the product is being used for motor fuel or as a petrochemical feedstock.

The following results of a pilot plant operation illustrate the advantages to be obtained through utilization of the subject invention. A high purity stream of propane was passed through a dehydrocyclodimerization reaction zone operated in accordance with the preferences set out herein and containing a catalyst comprising gallium on a support comprising a zeolite. The result was a 60 weight percent conversion of the propane to aromatic hydrocarbons. In a comparative example, employing the subject invention six mole percent benzene was added to the feedstream to the pilot plant with other conditions remaining unchanged. The result was an unexpected increase in average propane conversion to 66 weight percent with no loss in total aromatic selectivity by weight. It was also found that the total moles of aromatics formed using the process was lower but that more alkylbenzenes were produced with the benzene cofeed.

I claim as my invention:

1. In a hydrocarbon conversion process wherein a vapor phase feedstream comprising a $C_2$–$C_5$ aliphatic hydrocarbon is passed into a catalytic reaction zone containing a solid catalyst and converted into aromatic hydrocarbons comprising benzene, toluene and xylenes which are recovered from a reaction zone effluent stream; the improvement which comprises charging benzene and/or toluene into the reaction zone to increase the relative production of xylenes.

2. The improvement of claim 1 further characterized in that the aromatics charged to the reaction zone are recovered from an effluent stream emanating from the reaction zone.

3. The process of claim 1 further characterized in that the feed stream is rich in $C_3$ hydrocarbons.

4. The process of claim 1 further characterized in that the feed stream is rich in $C_4$ hydrocarbons.

5. In a dehydrocyclodimerization process wherein a vapor phase feedstream comprising propane or butane is passed into a reaction zone maintained at dehydrocyclodimerization conditions and a reaction zone effluent stream comprising benzene, toluene, xylenes and propane or butane is passed into a product recovery zone, and xylene is recovered as a product; the improvement which comprises recovering benzene from the reaction zone effluent stream and recycling benzene to the reaction zone.

6. The process of claim 5 further characterized in that a solid catalyst comprising a zeolite is employed within the reaction zone.

7. The process of claim 6 further characterized in that the catalyst comprises gallium.

8. The process of claim 7 further characterized in that the concentration of benzene in the hydrocarbons entering the reaction zone is from about 2.5 to about 8.0 mole percent.

9. A process for the production of aromatic hydrocarbons which comprises the steps of:
   (a) passing a first process stream comprising benzene and a feedstream comprising a $C_2$–$C_5$ aliphatic feed hydrocarbon into a reaction zone maintained at dehydrocyclodimerization conditions and containing a solid catalyst and producing a reaction zone effluent stream which comprises the feed hydrocarbon, benzene, toluene and xylenes; and,
   (b) separating the reaction zone effluent stream in a separation zone and producing a product stream comprising xylenes.

10. The process of claim 9 further characterized in that the feedstream is rich in $C_3$ hydrocarbons.

11. The process of claim 9 further characterized in that the feedstream is rich in $C_4$ hydrocarbons.

12. The process of claim 9 further characterized in that the catalyst comprises a zeolite.

13. The process of claim 12 further characterized in that the catalyst comprises gallium.

14. The process of claim 9 further characterized in that the separation zone effluent stream is separated by a series of steps which comprise fractional distillation and a benzene-rich second process stream is also produced, and in that at least a portion of the second process stream is passed into the reaction zone as the previously referred to first process stream.

15. The process of claim 14 further characterized in that the benzene-rich second process stream comprises toluene.

16. A dehydrocyclodimerization process which comprises the steps of:
   (a) passing a feedstream which comprises a $C_3$ or $C_4$ aliphatic hydrocarbon and a first process stream which comprises benzene into a dehydrocyclodimerization reaction zone maintained at dehydrocyclodimerization conditions and containing a solid catalyst comprising a zeolite and producing a reaction zone effluent stream comprising benzene, toluene and xylenes;
   (b) separating the reaction zone effluent stream by a series of steps comprising partial condensation and fractional distillation and producing a product stream comprising xylenes and a second process stream comprising benzene; and,
   (c) recycling at least a portion of the second process stream to the reaction zone as the previously referred to first process stream.

17. The process of claim 16 further characterized in that the catalyst comprises gallium.

18. The process of claim 17 further characterized in that the feedstream is rich in butanes.

19. The process of claim 16 further characterized in that the concentration of benzene in the hydrocarbons entering the dehydrocyclodimerization reaction zone is from about 2.5 to about 8.0 mole percent.

* * * * *